of preparing a water-soluble or water-dispersible pesticidal composition is described. The pesticidal composition is prepared in a continuous process by intimately mixing a Bronsted acid precursor of the pesticidally active compound with a Bronsted base under reaction conditions in an extruder. The reaction is performed with minimal solvent and under conditions where the water of reaction volatilizes during the course of the reaction.
United States Patent Chin et al.

Patent Number: 5,070,197
Date of Patent: Dec. 3, 1991

[54] DRY REACTIVE PROCESSING

[75] Inventors: James Chin, Cheshire; James B. Marshall, Southbury; Michael D. Drozdick, Terryville, all of Conn.; Fred C. Rosa, Wylie, Tex.; Frederick D. Judge, Cheshire, Conn.

[73] Assignee: Uniroyal Chemical Company, Inc., Middlebury, Conn.

[21] Appl. No.: 336,921

[22] Filed: Apr. 12, 1989

Related U.S. Application Data

[63] Continuation of Ser. No. 208,827, Jun. 15, 1988, abandoned, which is a continuation of Ser. No. 841,904, Mar. 20, 1986, abandoned.

[51] Int. Cl.$^5$ ............... C07D 273/16; C07D 285/16; C07D 209/48; C07F 9/38
[52] U.S. Cl. ........................... 544/11; 548/476; 562/17; 568/711; 544/240
[58] Field of Search ............... 544/11, 240; 548/476; 562/17; 568/711

[56] References Cited

U.S. PATENT DOCUMENTS

3,801,632  4/1974  Lademann et al. ............... 260/505

FOREIGN PATENT DOCUMENTS

1642967  6/1971  Fed. Rep. of Germany .
1488369  6/1967  France .
1354316  5/1974  United Kingdom .

*Primary Examiner*—John M. Ford
*Attorney, Agent, or Firm*—Glenn E. Karta

[57] ABSTRACT

A method of preparing a water-soluble or water-dispersible pesticidal composition is described. The pesticidal composition is prepared in a continuous process by intimately mixing a Bronsted acid precursor of the pesticidally active compound with a Bronsted base under reaction conditions in an extruder. The reaction is performed with minimal solvent and under conditions where the water of reaction volatilizes during the course of the reaction.

9 Claims, No Drawings

DRY REACTIVE PROCESSING

This is a continuation of application Ser. No. 208,827, filed June 15, 1988, now abandoned which is a continuation of application Ser. No. 841,904 filed Mar. 20, 1986, now abandoned.

BACKGROUND OF THE INVENTION

For many years pesticides, particularly herbicides, were sold as liquids, for example, in 5 gallon steel cans. These cans are very expensive and an environmental nuisance. As a result, it has become the practice to produce pesticides in a dry, flowable form so that the pesticides can be packaged in less expensive, disposable bags.

Three conventional methods for producing dry water-soluble or water-dispersible pesticidal material are in current use. All are at least two-step processes: water is added, the granules are formed and then the free water is driven off. In the primary prior art method, pan granulation, from about 5 to 10% free water is added to the pesticide before granulation, yielding a total water content, before drying, of from about 18 to 22%. Unfortunately, this process produces round particles which roll readily and disperse freely in the environment if bags are broken or accidentally spilled. Also, the particles of this process have a broad particle size spectrum, i.e., many fines and oversized particles, with overall bulk densities of from only about 22 to 28 pounds per cubic foot.

The second method used involves spray drying and the disadvantages of large volume equipment and low production rates. Furthermore, high energy input is needed to eliminate the large amount of water added during processing (up to 80%). Particles produced by this process are also spherical.

The third means of producing dry flowable material utilizes an extrusion wherein the pesticidal composition is mixed in an extruder, extruded through a die, and cut into pellets. No chemical reaction occurs in the extruder The products are usually composed of very hard, compact pellets which are undesirable for water-soluble formulations for the very hardness and compactness of the pellets make them difficult to dissolve.

Such procedures are described in U.S. Pat. Nos. 2,992,090; 3,062,637; 4,065,289; 4,374,082; and 4,435,383 and published U.K. Patent Application Nos. 2,094,624 and 2,109,687.

BRIEF DESCRIPTION OF THE INVENTION

In accordance with the instant invention, it has been discovered that the aforesaid disadvantages can be overcome by intimately admixing the Bronsted acid-form of the pesticide with a Bronsted base directly in a high shear mixing device, such as for example an extruder, essentially without the addition of an extraneous solvent. The reaction is performed continuously and directly in the extruder, the water of reaction being driven off by the resultant heat of reaction.

By using this dry reactive method, the end product can be formed in one step. The exothermic neutralization reaction takes place in the extruder and the moist product exits the extruder at a temperature sufficiently high to drive off the free water formed by the reaction or the small amount of water (usually about 4 wt.%) optionally added upstream for initial lubricity. Since constricting dies are not necessary, the pressure differential in a given zone rarely exceeds about 40 psi. Accordingly, the extruder does not need internal sealing means. The product has a relatively narrow particle size distribution, i.e., very few fines, granules of irregular shape, outstanding attrition resistance, and high bulk density (generally from about 38 to 44 pounds per cubic foot). Surprisingly, the water-soluble products are rapidly soluble in water.

The dry reactive processing of the invention is also particularly useful in the production of water-soluble foods and micro-nutrient granules, such as metal oxides and hydroxides with various organic acids (e.g., maleic acid).

In summary, superior solid products of dry water-dispersible or water-soluble pesticides can be formed directly without the attendant disadvantages of slurry processing. In addition to reducing energy consumption, the process is essentially free of dust, thereby reducing operator exposure, eliminating the need for complex ventilating equipment, and minimizing product loss.

Especially after reaching steady state conditions, the process may be readily adapted to computerized control yielding a product with a controlled moisture content and marked advantages over the batchwise process of the prior art.

DETAILED DESCRIPTION OF THE INVENTION

Pesticidal Bronsted acids suitable for being treated with Bronsted bases in accordance with this invention to form pesticidal salts may be insecticides, acaricides, miticides, aphicides, fungicides, bactericides, viricides, algicides, herbicides, growth regulators, rodenticides, repellents, and the like such as the following chemicals:

methyl 2,5-dimethyl-4,6-dioxo-5-[1-[(2-propyl-oxy)-amino]butylidene]cyclohexylcarboxylate,
3-adino-2,5-dichlorobenzoic acid,
2,3,6-trichlorobenzenacetic acid,
3,6-dichloro-2-methoxybenzoic acid,
3,6-dichloro-2-pyridinecarboxylic acid,
2-(1-methylpropyl)-4,6-dinitrophenol,
7-oxabicyclo[2.2.1]heptane-2,3-dicarboxylic acid,
2-(2,4,5-trichlorophenoxy)propionic acid,
N-(phosphonomethyl)glycine,
N,N-bis(phosphonomethyl)glycine,
2-[(1-naphthalenylamino)carbonyl]benzoic acid,
4-amino-3,5,6-trichloropyridine-2-carboxylic acid,
5-(2-chloro-4-trichloromethylphenoxy)-2-nitrobenzoic acid,
3-(1-methylethyl)-1H-2,1,3-benzothiadiazin-4(3H)-one 2,2-dioxide,
butanedioic acid mono(2,2-dimethylhydrazide),
2,3:4,6-bis-O-(1-methylethylidene)-alpha-L-xylo-2-hexulofuranosonic acid,
gibberellic acid,
4-(indol-3-yl)butyric acid,
1,2-dihydropyridazine-3,6-dione,
2-methyl-4,6-dinitrophenol,
2,4-dichlorophenoxyacetic acid,
2,4,5-trichlorophenoxyacetic acid,
2-methyl-4-chlorophenoxyacetic acid S-ethyl ether,
2-methyl-4-chlorophenoxyacetic acid,
4-(2-methyl-4-chlorophenoxy)butyric acid,
2-(2-methyl-4-chlorophenoxy)propionic acid,
4-(2,4 dichlorophenoxy)butyric acid,
methyl 5-(2,4 dichlorophenoxy)-2nitrobenzoate, 5-[chloro-4-(difluoromethyl)-phenoxy]-2-nitrobenzoate,
3,6-dichloro-O-anisic acid,
2,3,6-trichlorophenylacetic acid,
4-chloro-2-oxobenzothiazolin-3-ylacetic acid,
3,5,6-trichloro-2-pyridyl-oxyacetic acid,
4-amino-3,5,6-trichloropicolinic acid,
3,6-dichloropicolinic acid,
3-(p-chlorophenyl)-1,1-dimethylurea trichloroacetate,
3-phenyl-1,1-dimethylurea trichloroacetate,
methylarsonic acid,
dimethylarsonic acid,
2,2,3,3-tetrafluoropropionic acid,
(aminocarbonyl)phosphonic acid,
pentachlorophenol,
2,2-dichloropropionic acid,
trichloroacetic acid,
1-naphthaleneacetic acid,
2-(3-chlorophenoxy)propionic acid,
4-chlorophenoxy acetic acid,
3-trifluoromethyl-4-nitrophenol,
S-chloro-N-(2-chloro-4-nitrophenyl-2-hydroxybenzamide,
3-(alpha-acetonylfurfuryl)-4-hydroxy coumarin,
2-pivaloylevelane-1,3-dione.

Bronsted bases suitable for forming salts with the pesticidal acids include alkali metal hydroxides, alkaline earth metal hydroxides, ammonia and amines such as LiOH, NaOH, KOH, Mg(OH)$_2$, Ca(OH)$_2$, Ba(OH)$_2$, C$_2$H$_5$NH$_2$, (CH$_3$)$_3$N, (C$_2$H$_5$)$_2$NH, (C$_2$H$_5$)$_3$N, n-C$_3$H$_7$NH$_2$, (n-C$_3$H$_7$)$_2$NH; (i-C$_3$H$_7$)NH$_2$, (CH$_3$)$_2$N(i-C$_4$H$_9$), (CH$_3$)$_2$N(i-C$_5$H$_{11}$), C$_2$H$_5$NHC$_4$H$_9$, (HOC$_2$H$_4$)$_2$NH, (HOC$_2$H$_4$)$_3$N, HO(CH$_2$)$_3$NH$_2$, [HO(CH$_2$)$_3$]$_2$NH, C$_6$H$_5$NH$_2$, (C$_6$H$_5$)$_2$NH, C$_{10}$H$_7$NH (C$_{10}$H$_7$)$_2$NH, NH$_3$ and the like. Preferred bases are NaOH, KOH, Mg(OH)$_2$, Ba(OH)$_2$, Ca(OH)$_2$, (C$_2$H$_5$)$_2$NH, (C$_2$H$_5$)$_3$N, (HOC$_2$H$_4$)$_2$NH, (HOC$_2$H$_4$)$_3$N and NH$_3$, with NaOH, KOH, (C$_2$H$_5$)$_2$NH, (C$_2$H$_5$)$_3$N, (HOC$_2$H$_4$)$_2$NH and (HOC$_2$H$_4$)$_3$N being most preferred.

Usually, the pesticidal salts obtained by the process of this invention are solid materials at room temperature having melting temperatures considerably above those of the pesticidal acid precursors. However, the pesticidal Bronsted acids introduced into the extruder may be solid or liquid, and the Bronsted bases may be solid, liquid or gaseous. Preferably, the pesticidal acids are solids and the bases are solids, liquids, or solids dissolved in water at high concentrations (ca. 50-95%, weight).

In most cases, the reaction products are particles with a surprisingly narrow particle size distribution. Generally, such particles may be in a size of 1-50 mesh, preferably 2-40 mesh and most desirably 4-30 mesh, whereby at least 75%, preferably 85% and most preferably at least 90%, of the particles fall within the above limits.

Because of the generally exothermic nature of the reaction, it may be advisable to provide an inert material in admixture with the pesticidal Bronsted acid, the Bronsted base or both in order to serve as a so-called heat sink, taking up excess thermal energy. Suitable heat sink material includes inorganic fillers such as silicas, silicates such as fumed silica, ethyl cellulose, methyl cellulose, stearates, clays such as pyrophyllite clays, and diatomaceous earth. These materials may also serve as carriers and adsorbents for the pesticidal salts.

Where the heat sink material is water-insoluble, wetting agents and dispersants may be added to insure that the formulation is water-dispersible. The selection of such wetting agents and the amount added to the formulation are well known to those skilled in the art.

The amount of such inert filler used depends on the thermal energy to be controlled, the filler used, the filler's heat capacity and the concentration of final product desired. Water may be employed as well since it may serve simultaneously as a diluent for the Bronsted base, as a heat sink and as a lubricant. The amount of water added to the reactor may be determined by the exotherm to be controlled, the heat capacity of water and the amount of water to be driven off by the heat of reaction, taking into consideration also the amount of water produced by the reaction, if any.

In any case, it is advisable to determine on a small scale the feasibility of carrying out the reactions in the absence of a heat sink.

The residence time of ingredients in the extruder may be from 0.15 to 5 minutes, preferably from 0.25 to 3 minutes, usually from 0.5 to 2 minutes, at reaction temperatures ranging from 20° to 400° C., preferably from 40° to 350° C., most preferably from 75° to 250° C. It has been observed that it is desirable to conduct the reaction at from 3/10 to 9/10, preferably from 4/10 to 8/10, of the melting point (in Centigrade) of the pesticidal salt; e.g., when forming the sodium salt of N-(phosphonomethyl)glycine (m.p. 230° C., decomposes), the reaction temperature may be held advantageously at from 120° to 150° C., i.e., safely below the decomposition temperature.

Pressure conditions in the extruder may vary considerably depending on materials used, the product made, reaction temperatures, residence times, production rate and the equipment used, but generally relatively low pressures are required (a fact which enhances commercial feasibility of this process), with the final product and starting materials apparently being the major contributors to pressure development. The reaction pressures seldom exceed 100 psi.

The products obtained are essentially free of moisture; i.e., residual water levels ought not to exceed 15%, preferably 10%, most preferably 5% or less, all by weight.

Extruders that may be employed include: single screw extruders, planetary gear extruders, twin screw co-rotating extruders, twin screw counter-rotation extruders, two stage compounding extruders, kneader extruders, concentric screw mixer/extruders, reciprocating screw kneader/extruders, twin rotor continuous mix extruders, two stage mixer/extruders, disk extruders and transfer mixers.

While the primary objective of this invention is the preparation of solid, water-soluble or water-dispersible pesticidal salts, ingredients for formulation or dilution purposes, such as chelating agents, dispersants, surfactants, processing acids, fertilizer and trace metal nutrients, may be included to facilitate the reaction, promote increased water solubility, improve dispersion uniformity and/or enhance plant growth, it being understood that such ingredients may also contribute as heat sinks. Furthermore, the instant process is not limited to carrying out only one reaction at a time: two or more salts based on different pesticidal acids and/or different Bronsted bases may be prepared simultaneously. Also, depending on equipment used and product(s) made, addition of various ingredients to the extruder may be made at various extruder locations rather than all at the beginning of the extruder. More than one pass through the extruder may also be desirable.

EXAMPLE 1

A well-known herbicide, N-1-naphthylphthalamic acid (A) (see U.S. Pat. No. 2,556,665) and the sodium salt thereof (B) were prepared in accordance with the process of this invention.

(A) To a 30 mm co-rotating twin screw extruder (Werner & Pfleiderer ZSK type) was added at barrel 1 (of 14) 2370 g (16 mol) per hour phthalic anhydride in the form of crushed pellets, and at barrel 2 molten 1-naphthylamine at a rate of 2234 g (15.62 mol) per hour while maintaining a temperature profile of: zone 1=75°, zone 2=83°, zone 3=95°, zone 4= 75° and zone 5=45° C. At a screw speed of 300 rpm, the residence time was about 60 seconds, resulting in a product containing N-1-naphthylphthalamic acid (4365 g, ca. 96% yield based on 1-naphthylamine).

(B) N-1-naphthylphthalamic acid granules (about 2 mm diameter; containing about 5 wt. % phthalic acid and about 2 wt. % 1-naphthylamine), and ground sodium hydroxide (0.1 mm average diameter) were blended at a 1/1.25 molar ratio. Said mixture was fed to the extruder under conditions described in above procedure (A) except that all of the mixture was introduced at barrel 1 of the extruder at a feed rate of 6700 g per hour. The resulting product contained about 5750 g of the sodium salt of N-1-naphthylphthalamic acid indicating essentially stoichiometric conversion and exited the extruder as particles having an average diameter of 2 mm.

Under essentially the same extruder conditions, a higher (ca. 14 lbs/hr) rate was achieved in (B) than in (A) (ca. 10 lbs/hr). It is believed that the water formed by the acid-base reaction enhanced lubricity of the reaction mixture. The product was very soluble in water, causing the pH to rise to over 10 at 23 wt. % concentration.

EXAMPLE 2

Using a Brabender single screw (CWB Model No. 2003) extruder, a mixture of powdery N-(phosphonomethyl)glycine herbicide (see U.S. Pat. No. 3,799,758) and sodium hydroxide having an average diameter of 0.5 mm was reacted at a rate of about 50 g/minute with the temperature being controlled at about 130° C. throughout the extruder. The resultant product was completely water-soluble and had bulk density of 0.71 g/ml.

EXAMPLE 3

The herbicide 3-(1-methylethyl)-1H-2,1,3-benzothiadiazin-4(3H)-one 2,2-dioxide (see U.S. Pat. No. 3,822,257) was thoroughly mixed with sodium hydroxide (see Example 2) at a molar ratio of 1/1.1. Subsequently, the resultant mixture was fed to the Brabender extruder described in Example 2 with a 95° C. temperature setting throughout the extruder. The product was passed twice through the extruder, with the final product having a bulk density of 0.621 g/ml; it was completely water-soluble. Herbicidal activity was comparable to product made by prior art methods.

EXAMPLE 4

Employing the extruder of Example 1, the sodium salt of 2-(1-methylpropyl)-4,6-dinitrophenol (MPDP) herbicide was prepared in the presence of sodium salt of 1-naphthylphthalamic acid (NA-Na) by feeding to the extruder entrance 6900 g/hr the following mixture:

| Ingredient | Parts (weight) |
| --- | --- |
| NA—Na (88%) | 74.07 |
| NaOH (97%) | 5.86 |
| Dispersant | 13.16 |
| Chelating agent | 6.58 |
| Antifoaming agent | 0.33 |

Liquid MPDP at 2179 g/hr was fed to the center section of the extruder. The four sections of the extruder had the following temperature profile:

| Section 1 | 40° C. |
| --- | --- |
| Section 2 | 100° C. |
| Section 3 | 100° C. |
| Section 4 | 50° C. |

The resultant product exited the extruder in the form of a pasty solid having a moisture content of about 5 wt. % which upon cooling to room temperature was a friable solid readily crushable to the desired particle size. Herbicidal activity of the product mixture was essentially equivalent to the known commercial product, Dyanap ®.

Preparing the sodium salt of MPDP in the absence of a heat sink (such as the sodium salt of NA-Na) was unsuccessful because of overheating and flashing of the reaction mixture.

EXAMPLE 5

The potassium salt of 1,2-dihydropyridazine-3,6-dione (DHPD), a well-known plant growth regulator, is produced by reacting DHPD with potassium hydroxide using the equipment and procedure of Example 2. The reaction product exhibits excellent water solubility and plant growth regulating efficacy, equal to commercial solutions or solid formulations.

We claim:

1. A continuous extruder process for preparing a water soluble, irregularly shaped, granular salt having an activity selected from the group consisting of herbicide, plant growth regulant, insecticide, fungicide, acaricide and bactericide, and having a residual moisture content no greater than 10%, which comprises:

feeding a solid, precursor acid selected from the group consisting of N-1-naphthylphthalamic acid, N-(phosphonomethyl)-glycine, 3-(1-methylethyl)-1H-2,1,3-benzothiadiazin-4 (3H)-one 2,2-dioxide, 2-(1-methylpropyl)-4,6-dinitrophenol, and 1,2-dihydropyridazine-3,6-dione of said salt and the respective solid alkali metal or alkaline earth metal hydroxide base into one end of an extruder reaction zone without the addition of extraneous solvent;

intimately admixing the compounds under shear conditions sufficiently high to result in stoichiometric conversion to said salt having a bulk density from about 38 to about 44 pounds per cubic foot, with at least 75% of the salt particles being in the size of 1-50 mesh;

and removing the water-soluble, irregularly shaped, granular solid salt from the reaction zone.

2. The process of claim 1 wherein inert inorganic material is admixed with the compounds in the reaction zone to absorb at least part of the heat of reaction.

3. The process of claim 1 wherein water vapor is withdrawn from the reaction zone during the reaction.

4. The process of claim 1 wherein said base further comprises ammonia or an organic amine.

5. The process of claim 1 wherein the acid of the active compound is N-1-naphthylphthalamic acid.

6. The process of claim 1 wherein the acid of the active compound is N-(phosphonomethyl)glycine.

7. The process of claim 1 wherein the acid of the active compound is 3-(1-methylethyl)-1H-2,1,3-benzothiadiazin-4(3H)-one 2,2-dioxide.

8. The process of claim 1 wherein the acid of the active compound is 2-(1-methylpropyl)-4,6-dinitrophenol.

9. The process of claim 1 wherein the acid of the active compound is 1,2-dihydropyridazine-3,6-dione.

* * * * *